US009717556B2

(12) United States Patent
Sigmon, Jr.

(10) Patent No.: US 9,717,556 B2
(45) Date of Patent: Aug. 1, 2017

(54) COLLET FOR AN ENDOSCOPIC NEEDLE KNIFE

(71) Applicant: Cook Medical Technologies LLC, Bloomington, IN (US)

(72) Inventor: John Crowder Sigmon, Jr., Winston-Salem, NC (US)

(73) Assignee: Cook Medical Technologies LLC, Bloomington, IN (US)

( * ) Notice: Subject to any disclaimer, the term of this patent is extended or adjusted under 35 U.S.C. 154(b) by 181 days.

(21) Appl. No.: 14/134,181

(22) Filed: Dec. 19, 2013

(65) Prior Publication Data

US 2014/0180284 A1 Jun. 26, 2014

Related U.S. Application Data

(60) Provisional application No. 61/745,145, filed on Dec. 21, 2012.

(51) Int. Cl.
*A61B 18/14* (2006.01)
*A61B 90/00* (2016.01)
*A61B 18/16* (2006.01)

(52) U.S. Cl.
CPC .......... *A61B 18/1492* (2013.01); *A61B 90/03* (2016.02); *A61B 2018/144* (2013.01); *A61B 2018/1475* (2013.01); *A61B 2018/162* (2013.01); *A61B 2218/002* (2013.01)

(58) Field of Classification Search
CPC ............ A61B 19/30; A61B 2018/1475; A61B 2018/144; A61B 2018/162
USPC ................................... 606/41, 45–48; 607/99
See application file for complete search history.

(56) References Cited

U.S. PATENT DOCUMENTS

| 4,708,137 | A | 11/1987 | Tsukagoshi |
| 5,626,577 | A | 5/1997 | Harris |
| 5,827,280 | A | 10/1998 | Sandock et al. |
| 6,395,003 | B1 | 5/2002 | Ouchi |
| 6,702,812 | B2 | 3/2004 | Cosmescu |

(Continued)

FOREIGN PATENT DOCUMENTS

| JP | 5042166 A | 2/1993 |
| JP | 2009-090003 A | 4/2009 |

(Continued)

OTHER PUBLICATIONS

Japanese Office Action for corresponding Japanese Application No. 2013-264438 mailed Dec. 16, 2015 including translation.

(Continued)

*Primary Examiner* — Thomas Giuliani
(74) *Attorney, Agent, or Firm* — Brinks Gilson & Lione

(57) ABSTRACT

An endoscopic needle knife may include a collet coupled to a distal end of a tubular member of the needle knife. A cutting wire may be disposed within a cutting wire lumen of the tubular member and a central lumen of the collet. An inner surface of the collet body may create a frictional force between the cutting wire and the inner surface so that the cutting wire is resistant to longitudinal movement relative to the tubular member caused by external forces. The frictional force may also be less than a longitudinal force exerted on the cutting wire by a handle assembly or other control mechanism that is used to longitudinally move the cutting wire within the tubular member and the collet.

19 Claims, 3 Drawing Sheets

(56) References Cited

U.S. PATENT DOCUMENTS

| | | |
|---|---|---|
| 6,780,180 B1 * | 8/2004 | Goble ................ A61B 18/1206 606/41 |
| 7,135,018 B2 | 11/2006 | Ryan et al. |
| 8,048,073 B2 | 11/2011 | Nakamura et al. |
| 8,052,682 B2 | 11/2011 | Sugita |
| 2005/0215853 A1 | 9/2005 | Ouchi |
| 2008/0114353 A1 | 5/2008 | Sugita et al. |
| 2008/0122311 A1 * | 5/2008 | Werst ....................... H02K 1/30 310/216.004 |
| 2010/0217073 A1 | 8/2010 | Fischer et al. |
| 2011/0202007 A1 | 8/2011 | Leeflang et al. |

FOREIGN PATENT DOCUMENTS

| | | |
|---|---|---|
| JP | 2010-124913 A | 6/2010 |
| JP | 2010124913 | 10/2010 |

OTHER PUBLICATIONS

Extended European Search Report for corresponding EP Application No. 13199106.9.

* cited by examiner

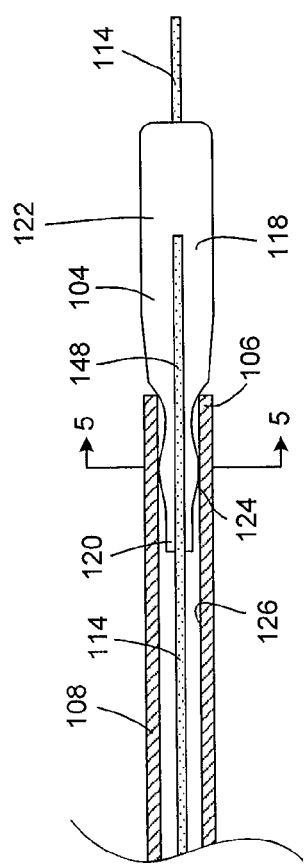
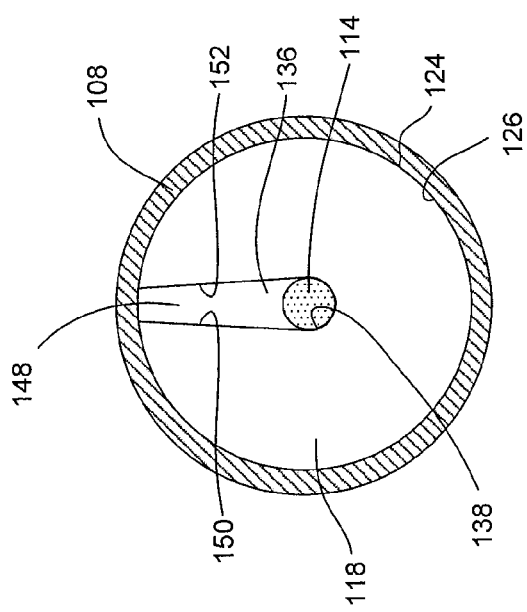

COLLET FOR AN ENDOSCOPIC NEEDLE KNIFE

CROSS-REFERENCE TO RELATED APPLICATION

The present application claims the benefit of U.S. Provisional Application No. 61/745,145, filed Dec. 21, 2012. The contents of U.S. Provisional Application No. 61/745,145 are hereby incorporated by reference in their entirety.

TECHNICAL FIELD

The present invention relates generally to medical devices, and more particularly to a collet coupled to a catheter of an endoscopic needle knife.

BACKGROUND

Endoscopic needle knives may be used to perform various electrosurgical medical procedures, such as endoscopic submucosal dissection (ESD) or endoscopic retrograde cholangiopancreatography (ERCP) on tissue within a patient. An endoscopic needle knife may be used as an alternative to a sphincterotome, particularly where the sphincterotome is unable to cannulate the papilla. The endoscopic needle knife may include a cutting wire disposed within a catheter. The cutting wire may be moved so that a distal end of the cutting wire distally extends past the catheter to a desired location. The distal end of the cutting wire may contact the tissue, and an electrical current may be sent along the cutting wire to perform the electrical procedure.

During operation of the endoscopic needle knife, various forces may be exerted on the endoscopic needle knife that may cause longitudinal movement of the cutting wire relative to the tubular member. For example, forces due to hysteresis as the needle knife moves between tortuous to straight positions within a working channel of the endoscope may cause the cutting wire to move. Additionally, the cutting wire may move when the distal end comes into contact with the tissue at the treatment site. Consequently, the distal end of the cutting wire may move or be displaced from its desired location, and the amount of cutting wire exposed at the distal end may uncontrollably vary.

BRIEF SUMMARY

An aspect of the present disclosure may include an endoscopic needle knife configured to perform an electrosurgical procedure at a treatment site within a patient. The endoscopic needle knife may include a cutting wire configured to conduct an electrical current to perform the electrosurgical procedure. The endoscopic needle knife may also include an elongate tubular member and a cutting wire lumen longitudinally extending through the tubular member and configured to receive the cutting wire. Additionally, a collet may be coupled to a distal end of the tubular member. The collet may include a collet body and a central lumen longitudinally extending through the collet body and configured to receive the cutting wire. The collet body may include an inner surface defined by the central lumen. The inner surface may exert an inward force on the cutting wire when the cutting wire is disposed within the central lumen of the collet.

Another aspect of the present disclosure may include a collet coupled to a catheter of an endoscopic needle knife. The collet may include a collet body that has a proximal portion configured to be coupled to a distal end of a tubular member of the endoscopic needle knife. The collet may also have a central lumen longitudinally extending through the collet body. The central lumen may be sized to have a cutting wire of the endoscopic needle knife movably disposed therein. An inner surface of the collet body may be defined by the central lumen. The inner surface may create a frictional force with the cutting wire when the proximal portion is coupled to the distal end of the tubular member. The frictional force may prevent longitudinal movement of the cutting wire caused by one or more external forces during operation of the endoscopic needle knife. Additionally, the collet may include a slit longitudinally disposed through the collet body. The slit may be in a closed position when the proximal portion of the collet body is coupled to the distal end of the tubular member.

A further aspect of the present disclosure may include a medical system that includes an endoscopic needle knife and a power source electrically coupled to the endoscopic needle knife to deliver electrical current to the endoscopic needle knife for performance of an electrosurgical procedure. The endoscopic needle knife may include an elongate tubular member, a cutting wire lumen longitudinally extending through the tubular member, and a collet coupled to a distal end of the tubular member. The collet may include a collet body and a central lumen longitudinally extending through the collet body. The collet body may include an inner surface defined by the central lumen. The endoscopic needle knife may also include a cutting wire that receives the electrical current from the power source to perform the electrosurgical procedure. The cutting wire may be disposed within the cutting wire lumen and the central lumen of the collet. Further, the endoscopic needle knife may include a handle assembly that has a control mechanism operatively coupled with the cutting wire to longitudinally move the cutting wire relative to the tubular member. The inner surface of the collet body may exert an inward force on the cutting wire to create a frictional force between the cutting wire and the inner surface. The frictional force may be greater than longitudinal external forces exerted on the cutting wire during operation of the endoscopic needle knife, and less than a longitudinal force exerted on the cutting wire by the control mechanism.

BRIEF DESCRIPTION OF THE DRAWINGS

FIG. 4 shows a side view of the collet of FIG. 1 coupled to the distal end of the tubular member of the endoscopic needle knife.

FIG. 5 shows a cross-sectional, axial view of the collet taken along line 5-5 in FIG. 4.

DETAILED DESCRIPTION

The present disclosure describes an endoscopic needle knife configured to perform an electrosurgical procedure that includes a collet coupled to a distal end of a catheter. To perform the electrosurgical procedure, a cutting wire may be advanced through the catheter and then through the collet, where a distal end of the cutting wire may be exposed. While the cutting wire is disposed within the collet, the collet may exert an inward force on the cutting wire, creating a frictional force that provides resistance to longitudinal movement of the cutting wire at the distal end.

The cutting wire may be subjected to external forces that longitudinally bias the cutting wire relative to the catheter. The external forces may include hysteretic forces or forces due to hysteresis created from movement of the catheter and cutting wire through a tortuous path within a patient. In addition or alternatively, the external forces may include forces created when the cutting wire makes contact with tissue at a treatment site within the patient. The collet may be coupled to the distal end of the catheter to prevent longitudinal movement of the cutting wire relative to the catheter caused by external forces. To prevent longitudinal movement caused by external forces, the frictional force created by the collet may be greater than a worst-case or maximum external force.

While preventing longitudinal movement of the cutting wire caused by external forces, the collet may permit longitudinal movement of the cutting wire due to a longitudinal force exerted on the cutting wire by a control mechanism of the needle knife that advances and retracts the cutting wire relative to the catheter. To permit movement of the cutting wire due to the control mechanism, the frictional force created by the collet may be less than the longitudinal force exerted on the cutting wire by the control mechanism. In this way, the collet may provide a frictional force that allows an operator to move the cutting wire to a desired position without external forces displacing the cutting wire away from the desired position during movement or operation of the needle knife.

The collet may be used with an endoscopic needle knife that has a monopolar configuration or a bipolar configuration. Where the needle knife has a bipolar configuration, the collet may part of a return path for electrical current used to perform the electrosurgical procedure.

Figure 1:
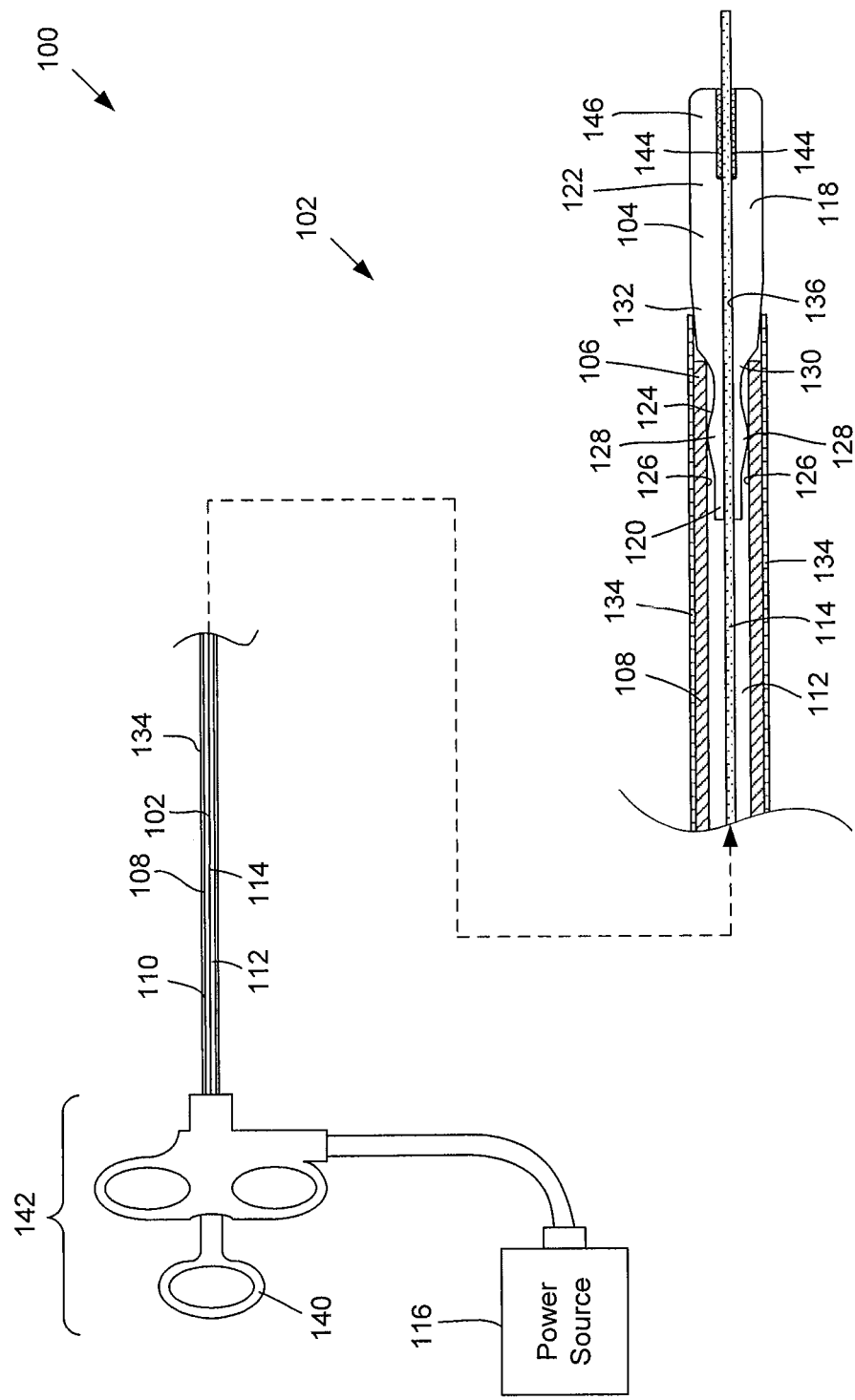
FIG. 1 shows a partial cross-sectional side view of an electrosurgical medical system 100 that includes an endoscopic needle knife having a collet.

FIG. 1 shows a partial cross-sectional side view of an electrosurgical medical system 100 that includes an endoscopic needle knife 102 having a collet 104 coupled to a distal end 106 of an elongate tubular member 108. A cutting wire lumen 112 may longitudinally extend within the tubular member 108 from a proximal end 110 to the distal end 106 of the tubular member 108. In some example embodiments, the cutting wire lumen 112 may be centrally disposed within the tubular member 108. The cutting wire lumen 112 may be configured to receive and have movably disposed within it a cutting wire 114 that may be configured to perform an electrosurgical procedure, such as ESD or ERCP. The cutting wire 114 may include a conductive portion made of a conductive material, such as stainless steel or tungsten, as examples. The conductive portion may be coated or encased in an insulating material, such as a Parylene coating or polytetrafluoroethylene (PTFE) heat shrink, except at a distal tip. In some examples, the distal tip may be about one millimeter in length. The cutting wire 114 may be electrically coupled to a power source 116, such as an electrosurgical unit (ESU), that supplies electrical current to the cutting wire 114 to perform the electrosurgical procedure. For some example endoscopic needle knives 102, the power source 116 may be operatively coupled to the cutting wire 114 through a handle assembly 142, as shown in FIG. 1, although other configurations are possible.

The collet 104 may include a collet body 118 having a proximal portion 120 and a distal portion 122. The collet 104 may be coupled to the distal end 106 of the tubular member 108 through a press fit or frictional fit between an outer surface 124 of the proximal portion 120 and an inner surface 126 of the tubular member 108. The inner surface 126 may be defined or determined by the cutting wire lumen 112. In one example embodiment, the proximal portion 120 may include a protruding portion 128 that may be press fit to the inner surface 126. The protruding portion 128 may include an area of the proximal portion 120 having the largest outer diameter of the proximal portion 120. The largest outer diameter of the proximal portion 120 may be greater than a diameter of the cutting wire lumen 112 at the distal end 106 to create the press fit. As shown in FIG. 1, the protruding portion 128 may be a rounded, spherical, or ball-like structure. In alternative example embodiments, the proximal portion 120 may include multiple protruding portions, and/or shaped structures other than rounded, spherical, or ball-like to create the press fit between the outer surface 124 of the proximal portion 120 of the collet 104 and the inner surface 126 of the tubular member 108.

A distal end 130 of the proximal portion 120 of the collet body 118 may include a tapered portion that may serve or function as a transition between the proximal portion 120 and the distal portion 122. The tapered portion 130 may taper proximally such that the outer diameter of the collet body 118 may distally increase or expand to a size that is greater than the diameter of the cutting wire lumen 112. In this way, the tapered portion 130 may provide a stop at which point the collet 104 may not further extend in the cutting wire lumen 112.

In the example embodiment of the collet 104 shown in FIG. 1, the distal portion 122 may be a portion of the collet body 118 that may be disposed outside of and distal to the tubular member 108 and/or the portion of the collet body 118 that is not press fit to the inner surface 126 of the tubular member 108. The distal portion 122 may have an outer diameter that is greater than the diameter of the cutting wire lumen 112, as well as the outer diameters of the proximal portion 120 of the collet body 118. In an alternative example embodiment of the collet 104, both the proximal portion 120 and the distal portion 122 of the collet body 118 may be disposed within the cutting wire lumen 112 when the collet 104 is coupled and press fit to the distal end 106 of the tubular member 108.

Additionally, in the example embodiment of the collet 104 shown in FIG. 1, the distal portion 122 may include a proximal end 132 that includes a tapered portion. Some example endoscopic needle knives 102 may include an outer sheath 134 that longitudinally extends over the tubular member 108. The tapered portion 132 may have an outer diameter that distally increases from a size that is smaller than an inner diameter of the outer sheath 134 to a size that is larger than the inner diameter of the outer sheath 134. In this way, the outer sheath 134 may extend over at least a portion of the proximal end 134, but may not extend over the entire distal portion 122 of the collet body 118. In alternative example embodiments, the distal portion 122 of the collet body 118 may be disposed entirely or at least mostly within the outer sheath 134. In other alternative example embodiments, the proximal end 132 may not be tapered, and/or the endoscopic needle knife 102 may not include an outer sheath 134. Various configurations are possible.

The collet 104 may further include a central lumen 136 that may longitudinally extend within the collet body 118 from the proximal portion 120 to the distal portion 122. When the collet 104 is coupled to the distal end 106 of the tubular member 108, the central lumen 136 may be concentric or substantially concentric with the cutting wire lumen 112 of the tubular member 112. The central lumen 136 may determine or define an inner surface 138 (shown in FIG. 3) of the collet body 118.

The central lumen 136 may be configured to receive and/or have the cutting wire 114 disposed within. When the proximal portion 120 is press fit to the inner surface 126 of the tubular member 108 and the cutting wire 114 is disposed in the central lumen 136 (as shown in FIG. 1), the inner surface 138 may pinch the cutting wire 114 and/or exert an inward force on the cutting wire 114, which may create a frictional force that provides resistance to longitudinal movement of the cutting wire 114 within the central lumen 136 of the collet 104. As previously described, the frictional force created by the collet may be greater than a maximum or worst-case external longitudinal force exerted on the cutting wire 114. By creating a frictional force that is greater than a maximum or worst-case external force, the collet 104 may prevent undesirable movement away from a desired position or location of the cutting wire 114 caused by an external force on the cutting wire 114.

The endoscopic needle knife 102 may further include a control mechanism 140 that may be operably coupled to the cutting wire 114 to longitudinally move the cutting wire 114 relative to the tubular member 108. In some example configurations, as shown in FIG. 1, the control mechanism 140 may be part of a handle assembly 142, although the control mechanism 140 may be separate from the handle assembly 142 in alternative configurations. The control mechanism 140 may be configured to longitudinally move the cutting wire 114 within the cutting wire lumen 112 and within the central lumen 136 of the collet 104.

The control mechanism 140 may be configured to move the cutting wire 114 in various ways. For example, the control mechanism 140 (such as the one shown in FIG. 1) may be configured to move longitudinally, such as by use of a slidable configuration, to move the cutting wire 114. Alternatively, rotational movement of the control mechanism 140, such by use of a threaded configuration, may longitudinally move the cutting wire 114. In addition or alternatively, the control mechanism 140 may include or be connected to one or more electronic devices (not shown) to move the cutting wire 114. Various configurations of the control mechanism 140, other than the configuration shown in FIG. 1, are possible.

To longitudinally move the cutting wire 114 when the cutting wire 114 is within the central lumen 136, either proximally or distally, the control mechanism 140 may exert a longitudinal force on the cutting wire 114 that is greater than the frictional force created by the collet 104. While creating a frictional force that is greater than a maximum or worst-case external force and less than the longitudinal force exerted on the cutting wire 114 by the control mechanism 140, the collet 104 may permit the control mechanism 140 to operate to longitudinally move the cutting wire 114 to a desired location or position without external forces moving the cutting wire away from the desired location or position.

The collet 104 may further include a ring or cannula 144 that may be disposed within the central lumen 136 at a distal end 146 of the collet 104. The cannula 144 may be included at the distal end 146 to enhance or maintain stability and/or concentricity of the cutting wire 114 at the distal end 146 of the collet 104. Additionally, the cannula 144 may be made of an insulative or dielectric material, such as polytetrafluoroethylene (PTFE) or polyimide (PI) as examples. In some example configurations, the collet body 118 may be made of a conductive material and, in addition, may be part of a return path for a bipolar configuration of the endoscopic needle knife 102. As previously described, the cutting wire 114 may be coated with an insulative material except at a distal tip, where the conductive portion of the cutting wire 114 may be exposed in order to perform the electrosurgical procedure. The cannula 144, made of an insulative or dielectric material, may be included at the distal end 146 to provide separation between the cutting wire 114 and the collet body 118 in order to prevent possible shorting between the cutting wire 114 (i.e., the active path) and the collet body 118 (i.e., the return path).

Figure 2:
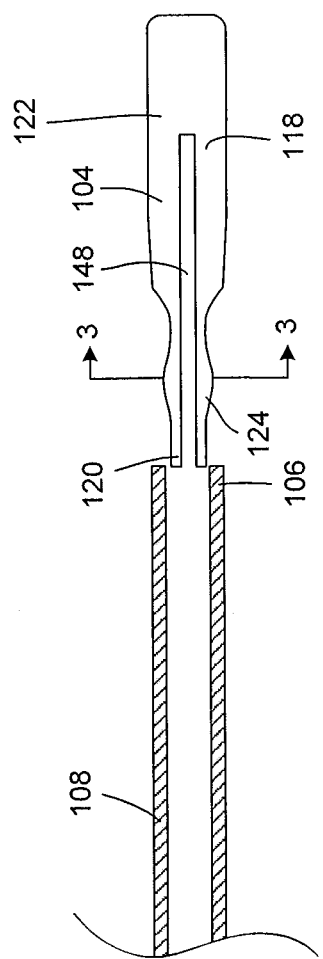
FIG. 2 shows a side view of the collet of FIG. 1 decoupled from a distal end of a tubular member of the endoscopic needle knife.

FIG. 2 shows a side view of the collet 104 decoupled from the proximal end 106 of the tubular member 108. As shown in FIG. 2, the collet 104 may further include a gap or slit 148 that longitudinally extends in the collet body 118. The slit 148 may extend from the proximal portion 120 to a position in the distal portion 122 that is proximal the distal end 146. In some example embodiments, a length of the slit 148 may be in a range of about 75 percent to 80 percent a total length of the collet 104, although other lengths may be used. Additionally, the slit 148 may extend in the collet body 118 from the outer surface 124 to the inner surface 138 (shown in FIG. 3).

The slit 148 may enable the collet body 118 to flex or move between an unbiased position and a biased position. The collet body 118 may be in the unbiased position when decoupled to the distal end 106 of the tubular member 108. The collet body 118 may be in the biased position when coupled and press fit to the distal end 106.

Figure 3:
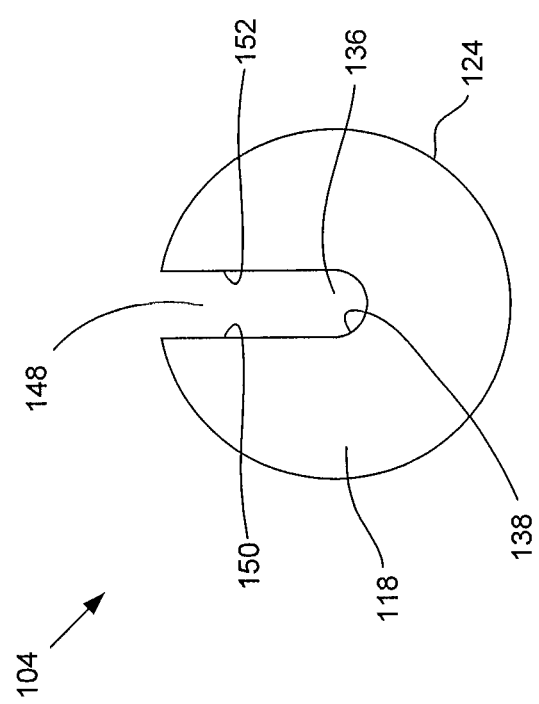
FIG. 3 shows a cross-sectional, axial view of the collet taken along line 3-3 in FIG. 2.

FIG. 3 shows a cross-sectional, axial view of the collet 104 taken along line 3-3 in FIG. 2. When the collet body 118 is in the unbiased position, the width of the slit 148, which may be defined by a distance between opposing side walls 150, 152 of the collet body 118 formed by the slit 148 may be at a maximum. In addition or alternatively, when the collet body 118 is in the unbiased position, a cross-sectional area of the central lumen 136 (i.e., a cross-sectional area defined by the inner surface 138 of the collet body 118) may be at a maximum.

Referring to FIG. 4, when the collet 104 is press fit to the tubular member 108, the inner surface 126 of the tubular member 108 may exert an inward bias on the outer surface 124 of the collet body 118, which may cause the slit 148 to close or be in a closed or substantially closed position—i.e., the press fit may cause the width of the slit 148 to decrease and the side walls 150, 152 of the collet body 118 separated by the slit 148 to move closer to each other. As a result, the inner surface 138 may move inward or contract, which may decrease the cross-sectional area of the central lumen 136. The resultant cross-sectional area of the central lumen 136 when the collet 104 is press fit to the tubular member 108 may be dimensioned relative and/or proportional to the diameter of the cutting wire 114 such that a frictional force between the inner surface 138 and the cutting wire 114 is created when the cutting wire 138 is inserted and/or moved within the central lumen 136. As previously described, the frictional force may a value or within a range that is less than a longitudinal force exerted on the cutting wire 114 by the control mechanism 140, while greater than a maximum or worst-case external force to cause longitudinal movement of the cutting wire 114 relative to the tubular member 108.

FIG. 5 shows a cross-sectional, axial view of the collet 104 press fit to the tubular member 108, taken along line 5-5 in FIG. 4. When the collet 104 is press fit to the tubular member 108, the inward force exerted on the outer surface 124 by inner surface 126 of the tubular member 108 may cause the side walls 150, 152 to move closer to each other and the inner surface 138 to contract, thereby decreasing the cross-sectional area of the central lumen 136. The resultant cross-sectional area may be dimensioned relative and/or proportional to the diameter of the cutting wire 114 so that a frictional force is created between the inner surface 138 and the cutting wire 114.

In some example embodiments of the endoscopic needle knife 102, the cutting wire lumen 112 and the central lumen 136 and/or the slit 148 may be used as a flushing channel or lumen to send liquid or fluid to the treatment site, in addition to being used as a channel to advance and retract the cutting wire 114. For these example embodiments, when the collet 104 is press fit to the tubular member 108, a space defined by the central lumen 136 and/or the slit 148 that is unoccupied by the cutting wire 114 may be sufficient for the fluid to pass to the treatment site while still providing sufficient resistance against longitudinal movement of the cutting wire 114 due to external forces. During operation, the fluid may be passed through the cutting wire lumen 112 and the central lumen 112, and around or over the cutting wire 114 to the treatment site. In some configurations, the cutting wire 114 may occupy about 25 percent of the space or potential area within the collet body 118 for the fluid to pass.

The following describes an operation of the needle knife 102 to perform an electrosurgical procedure with reference to FIGS. 1-5. During operation of the endoscopic needle knife 102, the tubular member 108 with the collet 104 coupled (e.g., press fit) to the distal end 106 may be distally advanced to a treatment site within a patient, such as by being moved through a working channel of an endoscope (not shown). While the tubular member 108 and the collet 104 are being advanced, the cutting wire 114 may be disposed within the cutting wire lumen 112 of the tubular member 108. During advancement, the distal end of the cutting wire 114 may be disposed within the central lumen 136 of the collet 104, or alternatively may be disposed at a location proximal the collet 104 within the cutting wire lumen 112.

The tubular member 108 and the collet 104 may be advanced to a location near the treatment site that is visible by a camera of the endoscope (now shown). The cutting wire 114 may then be distally moved relative to the tubular member 108 using the control mechanism 140. The distal end of the cutting wire 114 may be moved through the cutting wire lumen 112 and through the central lumen 136 of the collet 104 to a desired location that is exposed outside of and distal to the distal end 146 of the collet 104. If necessary, the tubular member 108, the collet 108, and the cutting wire 114 may further be distally advanced so that the distal end of the cutting wire 114, now exposed, makes contact with tissue at the treatment site.

When the distal end of the cutting wire 114 is exposed outside of the collet 104, the electrosurgical procedure may be performed on the tissue. The power source 116 may be activated, which may send electrical current along the cutting wire 114, through the tissue at the treatment site, and then along a return path back to the currents source 116. Where the endoscopic needle knife 102 has a bipolar configuration, the electrical current, after passing through the tissue, may pass through the collet body 118, which may be part of the return path. Alternatively, where the endoscopic needle knife 102 has a monopolar configuration, the collet 104 may not be part of the return path, and the electrical current may pass through a return path that is outside of the patient.

While the cutting wire 114 is exposed outside of the collet 104 at a desired location, various forces may be longitudinally exerted on the cutting wire 114, such as forces due to hysteresis caused by movement of the tubular member 108 and/or contact from the tissue at the treatment site. However, the cutting wire 114 may be resistant to these external forces due to the frictional force created by the collet 104 on the cutting wire 114. As a result, the cutting wire 114 may remain in the desired location outside of the collet 104 in the presence of the external forces when the electrosurgical procedure is being performed.

After the electrosurgical procedure is performed, the power source 116 may be deactivated, and the distal end of the cutting wire 114 may be retracted back into the central lumen 114 and the cutting wire lumen 112 using the control mechanism 140. The tubular member 108, along with the collet 104 and the cutting wire 114, may then be removed from the patient.

The collet 104 may be made of various materials and/or be sized to have various dimensions. In some example embodiments, the collet 104 may be made of stainless steel, particularly for an endoscopic needle knife 102 having a bipolar configuration, although other materials, including conductive or non-conductive materials, may be used. For example, a metal other than stainless steel may be used, which may have a lower resistivity and/or better conduction than stainless steel. The dimensions of the collet 104 may be dependent on the type of endoscopic needle knife 102, the catheter 108, the cutting wire 114, and/or their respective dimensions. As non-limiting examples, a total length of the collet 104 may be about 0.46 inches; a length of the proximal portion 120 may be about 0.18 inches, and a length of the distal portion 122 may 0.28 inches. A largest diameter at the protruding portion 128 may be about 0.045 inches, and a largest diameter of the distal portion 122 may be about 0.045 inches.

Additionally, during design of the collet 104, the outer diameter of the protruding portion 128 and the width of the slit 148 may be dimensioned dependently of each other to obtain a desired frictional force and/or a desired press fit. In addition or alternatively, the width of the slit 148 may be dependent on the insulative material, such as PTFE heath shrink, covering the conductive portion of the cutting wire 114. For some example embodiments, the width of the slit 148 and/or the size of the central lumen 138 may be sized to be about the same size as or slightly larger than the diameter of the cutting wire 114 when the collet 104 is decoupled from the distal end 106 of the tubular member 108. Then, when the collet 104 is press fit to the tubular member, the space within the central lumen 138 contracts to achieve the desired amount of frictional force.

Additionally, the collet 104 described above with reference to FIGS. 1-5 is described as having a central lumen 138 that is concentric with a single cutting wire lumen 112 when the collet 104 is coupled to a tubular member 108. The collet 104 may alternatively be adapted to be coupled a tubular member 108 where the cutting wire lumen 112 is one of multiple lumens extending within the tubular member 108. The dimensions of the collet 104 may be adapted accordingly.

Further, the collet 104 may be considered a component of the endoscopic needle knife 102, or alternatively may be considered a component that is separate from and/or that is used with an endoscopic needle knife 102. For example, the endoscopic needle knife 102 may be manufactured to include and/or be delivered to an end user, operator, or purchaser, with the collet 104 coupled to the tubular member 108. Alternatively, the collet 104 may be a standalone component that is manufactured separate from and/or separately delivered to an end user or purchaser of the endoscopic needle knife 102. In some situations, the collet 104 may be a replaceable component. For example, the collet 104 may be replaced with a different collet. In addition or alternatively, for some example embodiments of the collet, the same collet may be used with different endoscopic needle knives, or with the same needle knife at different times or during different procedures. Various configurations are possible.

The foregoing description of various embodiments of the invention has been presented for purposes of illustration and description. It is not intended to be exhaustive or to limit the invention to the precise embodiments disclosed. Numerous modifications or variations are possible in light of the above teachings. The embodiments discussed were chosen and described to provide the best illustration of the principles of the invention and its practical application to thereby enable one of ordinary skill in the art to utilize the invention in various embodiments and with various modifications as are suited to the particular use contemplated. All such modifications and variations are within the scope of the invention as determined by the appended claims when interpreted in accordance with the breadth to which they are fairly, legally, and equitably entitled.

The invention claimed is:

1. An endoscopic needle knife configured to perform an electrosurgical procedure at a treatment site within a patient, the endoscopic needle knife comprising:
   a cutting wire configured to conduct an electrical current to perform the electrosurgical procedure;
   an elongate tubular member;
   a cutting wire lumen longitudinally extending through the tubular member and configured to receive the cutting wire; and
   a collet press fit to a distal end of the tubular member, the collet comprising:
      a collet body; and
      a central lumen longitudinally extending through the collet body and configured to receive the cutting wire,
      wherein the collet body comprises an inner surface defined by the central lumen, and
   wherein the inner surface of the collet body exerts an inward force on the cutting wire when the cutting wire is disposed within the central lumen of the collet to create a frictional force that provides resistance to longitudinal movement of the cutting wire at the distal end, and
   wherein a cross-sectional area of the central lumen is dimensioned relative to a diameter of the cutting wire such that when the collet is press fit to the distal end and the cutting wire is disposed within the central lumen, the frictional force that is created is within a range having a lower bound force value and an upper bound force value, wherein the lower bound force is greater than a maximum external longitudinal force to cause longitudinal movement of the cutting wire relative to the tubular member during operation of the needle knife, and wherein the upper bound force value is less than a longitudinal force exerted on the cutting wire by a control mechanism of the needle knife that is operatively coupled to the cutting wire, and
   wherein the collet body is dimensioned relative to the tubular member so that the press fit between the collet and the distal end of the tubular member causes a reduction in the cross-sectional area of the central lumen for creation of the frictional force in the range.

2. The endoscopic needle knife of claim 1, wherein the maximum external longitudinal force that the lower bound force of the range is greater than is a maximum force capable of being generated from at least one of: movement of the tubular member within a working channel of an endoscope or contact of the cutting wire with tissue at the treatment site.

3. The endoscopic needle knife of claim 1, wherein the cutting wire lumen defines an inner surface of the tubular member, and wherein the collet body comprises a proximal portion that is press fit with the inner surface of the tubular member to couple the collet to the distal end of the tubular member.

4. The endoscopic needle knife of claim 3, wherein the proximal portion of the collet body comprises a protruding portion that is press fit with the inner surface of the tubular member.

5. The endoscopic needle knife of claim 4, wherein the protruding portion comprises a rounded portion having an outer diameter that is larger than an inner diameter of the tubular member.

6. The endoscopic needle knife of claim 1, wherein the collet comprises a slit longitudinally extending in the collet body, wherein the slit is substantially closed when the collet is press fit to the distal end of the tubular member, the inner surface exerting the inward force on the cutting wire when the slit is substantially closed.

7. The endoscopic needle knife of claim 6, wherein the press fit between a proximal portion of the collet body and an inner surface of the tubular member substantially closes the slit.

8. The endoscopic needle knife of claim 6, wherein the slit longitudinally extends from a proximal end of the collet to a position proximal a distal end of the collet.

9. The endoscopic needle knife of claim 6, wherein the slit longitudinally extends a length that is within a range of about seventy-five to eighty percent of a length of the collet.

10. The endoscopic needle knife of claim 1, wherein the collet further comprises a cannula disposed in the central lumen at a distal end of the collet.

11. The endoscopic needle knife of claim 10, wherein the cannula is made of an insulating material.

12. The endoscopic needle knife of claim 1, wherein the endoscopic needle knife comprises a bipolar needle knife, and wherein the collet comprises a part of a return path of the bipolar needle knife.

13. The endoscopic needle knife of claim 1, wherein the central lumen of the collet is part of a flushing lumen, wherein during operation of the needle knife, fluid passes through the central lumen and around the cutting wire to the treatment site.

14. The endoscopic needle knife of claim 1, wherein the collet is made of stainless steel.

15. The endoscopic needle knife of claim 1, wherein the central lumen of the collet is concentric with the cutting wire lumen.

16. A collet configured to be coupled to a catheter of an endoscopic needle knife, the collet comprising:
   a collet body comprising a proximal portion configured to be press fit to a distal end of a tubular member of the endoscopic needle knife; and
   a central lumen longitudinally extending through the collet body, the central lumen sized to have a cutting wire of the endoscopic needle knife movably disposed therein,
   wherein the collet body comprises an inner surface defined by the central lumen, the inner surface creating a frictional force with the cutting wire when the proximal portion is press fit to the distal end of the tubular member, the frictional force providing resistance to longitudinal movement of the cutting wire at the distal end of the tubular member, wherein a cross-sectional area of the central lumen is dimensioned relative to a diameter of the cutting wire such that when the collet body is press fit to the distal end and the cutting wire is disposed within the central lumen, the frictional force that is created is within a range that is greater than a maximum external longitudinal force to cause longitudinal movement of the cutting wire relative to the tubular member during operation of the needle knife, and less than a longitudinal force exerted on the cutting wire by a control mechanism of the needle knife that is operatively coupled to the cutting wire, and wherein the collet body is dimensioned relative to the tubular member so that the press fit between the collet and the distal end of the tubular member causes a reduction in the cross-sectional area of the central lumen for creation of the frictional force.

17. A medical system comprising an endoscopic needle knife and a power source electrically coupled to the endoscopic needle knife to deliver electrical current to the endoscopic needle knife for performance of an electrosurgical procedure, the endoscopic needle knife comprising:

an elongate tubular member;

a cutting wire lumen longitudinally extending through the tubular member;

a collet coupled to a distal end of the tubular member, the collet comprising:
a collet body; and
a central lumen longitudinally extending through the collet body,
wherein the collet body comprises an inner surface defined by the central lumen;

a cutting wire that receives the electrical current from the power source to perform the electrosurgical procedure, the cutting wire disposed within the cutting wire lumen and the central lumen of the collet; and a handle assembly comprising a control mechanism operatively coupled with the cutting wire to longitudinally move the cutting wire relative to the tubular member, wherein the inner surface of the collet body exerts an inward force on the cutting wire to create a frictional force between the cutting wire and the inner surface, wherein the frictional force is greater than longitudinal external forces capable of being exerted on the cutting wire during operation of the endoscopic needle knife, and less than a longitudinal force that the control mechanism is configured to exert on the cutting wire, and wherein the collet body is dimensioned relative to the tubular member so that the coupling between the collet and the distal end of the tubular member causes a reduction in the cross-sectional area of the central lumen for creation of the frictional force.

18. The medical system of claim 17, wherein a proximal portion of the collet body is press fit to an inner surface of the cutting wire lumen of the tubular member.

19. A medical device comprising:

an elongate tubular member;

an inner member lumen longitudinally extending through the tubular member;

an elongate inner member longitudinally extending and movably disposed in the inner member lumen;

a collet press fit to a distal end of the tubular member, the collet comprising:
a collet body; and
a central lumen longitudinally extending through the collet body and configured to receive the elongate inner member,
wherein the collet body comprises an inner surface defined by the central lumen, and wherein the inner surface of the collet body exerts an inward force on the elongate inner member when the elongate inner member is disposed within the central lumen of the collet to create a frictional force that provides resistance to longitudinal movement of the inner member at the distal end, and wherein a cross-sectional area of the central lumen is dimensioned relative to a diameter of the inner member such that when the collet is press fit to the distal end and the inner member is disposed within the central lumen, the frictional force that is created is within a range that is greater than a maximum external longitudinal force to cause longitudinal movement of the inner member relative to the tubular member during operation of the medical device, and less than a longitudinal force exerted on the inner member by a control mechanism of the medical device that is operatively coupled to the inner member, and wherein the collet body is dimensioned relative to the tubular member so that the press fit between the collet and the distal end of the tubular member causes a reduction in the cross-sectional area of the central lumen for creation of the frictional force in the range.

* * * * *